United States Patent [19]

Heyse et al.

[11] Patent Number: 5,648,178
[45] Date of Patent: Jul. 15, 1997

[54] REACTOR SYSTEM STEEL PORTION

[75] Inventors: John V. Heyse, Crockett; Alan G. Kunze, El Cerrito, both of Calif.

[73] Assignee: Chevron Chemical Company, San Ramon, Calif.

[21] Appl. No.: 365,855

[22] Filed: Dec. 28, 1994

Related U.S. Application Data

[63] Continuation-in-part of Ser. No. 269,764, Jul. 1, 1994, Pat. No. 5,575,902, which is a continuation-in-part of Ser. No. 177,822, Jan. 4, 1994.

[51] Int. Cl.$^6$ .................................................. B32B 15/18
[52] U.S. Cl. ........................ 428/627; 428/664; 428/667; 422/240
[58] Field of Search .................. 428/610, 627, 428/667, 629, 614, 664, 665, 663; 422/240, 241

[56] References Cited

U.S. PATENT DOCUMENTS

| | | | |
|---|---|---|---|
| 1,802,695 | 4/1931 | Bennett | 428/667 |
| 2,063,596 | 12/1936 | Feilen | 196/133 |
| 2,685,543 | 8/1954 | Sindeband | 420/667 |
| 3,108,013 | 10/1963 | Chao et al. | 426/667 |
| 3,505,028 | 4/1970 | Douthit | 422/241 |
| 3,536,776 | 10/1970 | Lo | 260/683 |
| 3,623,901 | 11/1971 | Forstmann et al. | 428/667 |
| 3,634,147 | 1/1972 | Helwig | 426/667 |
| 3,743,551 | 7/1973 | Sanderson | 428/667 |
| 3,944,396 | 3/1976 | Chivinsky | 428/667 |
| 4,013,487 | 3/1977 | Ramqrist et al. | 148/16.5 |
| 4,297,150 | 10/1981 | Foster et al. | 148/6.3 |
| 4,404,087 | 9/1983 | Reed et al. | 208/48 AA |
| 4,444,732 | 4/1984 | Konoki et al. | 422/241 |
| 4,467,016 | 8/1984 | Baldi | 428/595 |
| 4,481,264 | 11/1984 | Faure | 428/667 |
| 4,555,326 | 11/1985 | Reid | 208/48 R |
| 4,685,427 | 8/1987 | Tasson et al. | 122/511 |
| 4,863,892 | 9/1989 | Porter et al. | 502/170 |
| 4,976,932 | 12/1990 | Maeda et al. | 422/240 |
| 5,118,028 | 6/1992 | Ogawa et al. | 226/194 |
| 5,242,665 | 9/1993 | Maeda et al. | 422/240 |

FOREIGN PATENT DOCUMENTS

| | | |
|---|---|---|
| 1604604 | 12/1981 | United Kingdom . |
| WO92/15653 | 9/1992 | WIPO . |

OTHER PUBLICATIONS

J. Shinohara et al., "Development of Nondestructive Technique for Measuring Carburization Thickness and of a New Carburization Resistant Alloy," Werkstoffe und Korrozion 37, (no month 1986), pp. 410–411.

*Primary Examiner*—John Zimmerman
*Attorney, Agent, or Firm*—Witta O. Priester

[57] ABSTRACT

Methods for cracking hydrocarbons in reactor systems having improved resistances to carburization and coking. The reactor system comprises a steel portion having provided thereon a Group VIB metal protective layer to isolate the steel portion from hydrocarbons, applied to a thickness effective for isolating the steel portion from the hydrocarbon environment. The protective layer is anchored to the steel substrate through an intermediate carbide-rich, bonding layer.

6 Claims, 1 Drawing Sheet

FIGURE
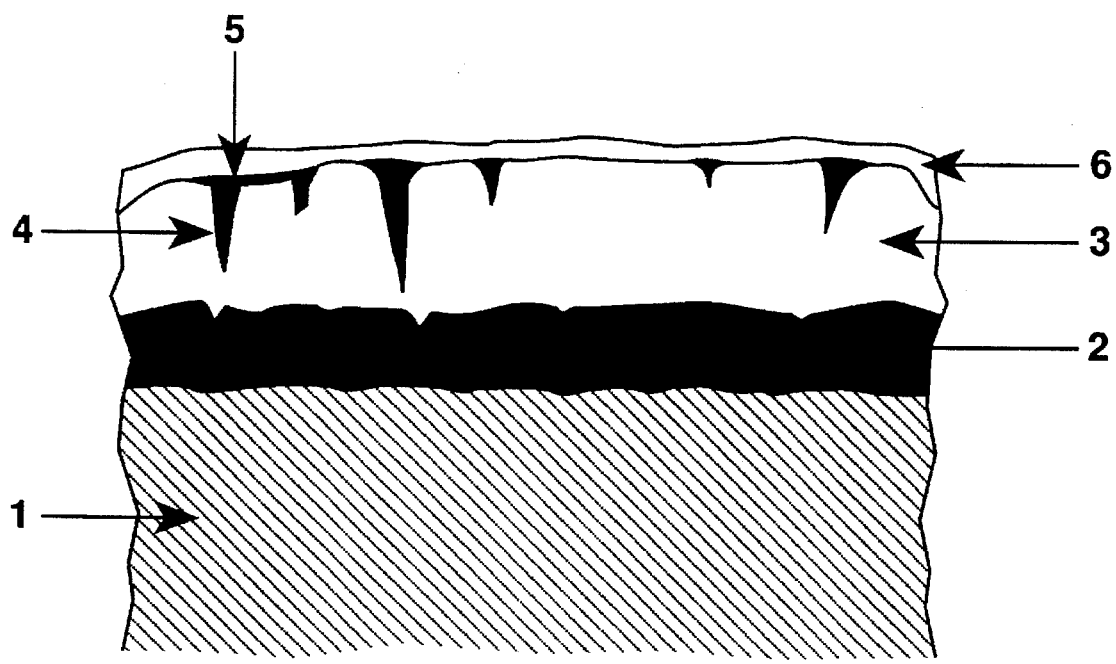

REACTOR SYSTEM STEEL PORTION

BACKGROUND OF THE INVENTION

This application is a continuation-in-part of application Ser. No. 08/269,764 filed Jul. 1, 1994, now U.S. Pat. No. 5,575,902, which is a continuation-in-part of application Ser. No. 08/177,822, filed Jan. 4, 1994. The contents of both these applications are hereby incorporated by reference.

The invention relates to processes for the cracking of hydrocarbons, particularly for the thermal cracking of a gaseous stream containing hydrocarbons. In part, the invention relates to the production of ethylene by cracking hydrocarbons in the presence of steam, and the prevention of coking associated with this process.

In thermal cracking operations a diluent fluid such as steam is usually combined with a hydrocarbon feed such as ethane and/or propane and/or naphtha, and introduced into a cracking furnace. Within the furnace, the feed stream which has been combined with the diluent fluid is converted to a gaseous mixture which primarily contains hydrogen, methane, ethylene, propylene, butadiene, and small amounts of heavier gases. At the furnace exit this mixture is cooled to remove most of the heavier gases, and then compressed. The compressed mixture is routed through various distillation columns where the individual components such as ethylene are purified and separated.

One recognized problem in thermal cracking is the formation of coke. Because coke is a poor thermal conductor, as coke is deposited higher furnace temperatures are required to maintain the gas temperature in the cracking zone at necessary levels. Higher temperatures increase feed consumption and shorten tube life. Also, cracking operations are typically shut down periodically to burn off deposits of coke. This downtime adversely affects production.

Another problem in thermal cracking is the embrittlement of the steel walls in the reaction system. Such embrittlement is due to carburization of the system metallurgy, and ultimately leads to metallurgical failure.

A variety of solutions have been proposed for addressing the problem of coke formation and carburization in thermal cracking processes. Many of these are associated with using novel steel types, especially alloys. See for example, U.S. Pat. No. 4,762,681 to Tassen et at. and U.S. Pat. No. 4,976,932 to Maeda et at. Others utilize antifoulants, for example, U.S. Pat. No. 4,507,196 to Reed et at. which describes certain chromium antifoulants, and antifoulants which are combinations of chromium and tin, antimony and chromium, and tin, antimony and chromium. These patents are incorporated herein by reference.

Some prior art processes, such as those that heat chromium compounds at high temperatures in air, produce chromium oxide coatings instead of metallic chromium coatings. This is undesirable, since in the presence of steam and hydrocarbons these oxides are acidic and produce coke. Other processes result in chromium carbide at the coating surface, without a protective overlaying of metallic chromium.

The use of chromium in coatings for steel protection is known. GB 1,604,604 to Perugini et al., discloses processes for protecting metal surfaces against corrosion by carburization at high temperatures and corrosion by oxidation. Example 15 shows an HK-40 steel coated with a chromium layer provided by plasma spray deposition. This layer is then painted with 10% $B_4C$ and 90% SiC. Example 16th cylinder (p. 4) also shows chromium applied to steel. In GB 1,149, 163 to ICI, methods of protecting against carburization are described. Here steels containing iron, chromium and nickel are coated with aluminum, chromium or nickel. This patent claims furnace tubes for ethylene crackers. It focuses on and exemplifies aluminising; however, chromising is also disclosed.

In King et at, "The Production of Ethylene by the Decomposition of n-Butane; the Prevention of Carbon Formation by the Use of Chromium Plating", Trans. of the E.I.C., 3, #1, 1 (1959), there is described an application of a 3/1000 inch thick (3 mil) chromium plate to a stainless steel reactor. This chromium plate is described as peeling-off the surfaces of the steel after a period of several months of operation, which was attributed to the high temperatures required for the reaction, and periodic heating and cooling.

SUMMARY OF THE INVENTION

Accordingly, one object of the invention is to provide an improved method for the cracking of hydrocarbons, where catalytic coking is minimized, and carburization in the reactor system is reduced.

Among other factors the invention is based on the discovery that a chromium protective layer effective for resisting carburization and coking, can be provided on a portion, or portions of the reactor system exposed to hydrocarbons, which, unlike prior art chromium layers, is resistant to peeling.

According to this invention an intermediate bonding layer is used which anchors the chromium protective layer to the steel substrate to be protected. In this regard, the reactor system comprises a steel portion, preferably a heat-resistant steel portion, having provided thereon a chromium protective layer to isolate the steel portion from hydrocarbons, applied to a thickness effective for completely isolating the steel portion from the hydrocarbon environment. The protective layer is anchored to the steel substrate through an intermediate carbide-rich, bonding layer.

Cracks have been observed to form in chromium protective layers, especially after the initial heating of an electroplated material. These cracks can allow steam (which is typically present) to attack the steel/chromium interface and undermine the chromium protective layer. According to another embodiment of the invention there is provided a novel procedure which includes a step of treating a chromium coated surface with hydrocarbons in the absence of steam which produces a metal carbide filler of the cracks which effectively seals-off the chromium coating and carbide-rich bonding layer from steam attack.

In yet another embodiment of the invention, a protective layer is formed by bonding a chromium layer to steel in the presence of a nitrogen-containing compound at elevated temperature. This has the advantage of forming not only a carbide-rich bonding layer, but also results in the filling of cracks in the chromium layer with chromium nitride which effectively seals off the carbide-rich bonding layer from steam attack.

An effective protective layer must resist deleterious chemical alteration, as well as peeling. Additionally, the protective layer must maintain its integrity through operation. As such, the protective coating must be sufficiently abrasion resistant during start-up and operation. The chromium-based coatings according to the invention have these advantages.

Preferably, the chromium protective layer is applied by a plating process such as electroplating, followed by curing. It can also be applied as a reducible paint which upon curing in a H$_2$-rich (or pure) environment, in the absence of steam, forms a continuous chromium metal layer of substantial thickness, indistinguishable from electroplated material, except that it is virtually free of cracks. It is very finely and cleanly anchored to the underlying steel through a carbide-rich bonding layer. Chromium paint protection can be applied and cured in-situ to an existing plant.

Moreover, a chromium paint such as that described above can be applied to a previously chromium-plated surface. The curing treatment for the paint causes chromium metal to fill cracks in the plate as they form, thereby producing a smooth, substantially crack-free chromium coating. The paint can also be used to repair damaged, previously chromium-plated steel. The chromium paints are especially useful to treat welds and other hard to reach areas that are otherwise untreatable by plating.

With the foregoing, as well as other objects, advantages, features and aspects of the disclosure that will become hereinafter apparent, the nature of the disclosure may be more clearly understood by reference to the detailed description and the appended claims.

BRIEF DESCRIPTION OF THE DRAWING

The drawing schematically illustrates the various metallic layers that are produced on a base construction material (1) of HP-50 steel after the steel has been plated with chromium, heat treated in nitrogen at 1800° F. for 2 hours (nitrogen curing) and then subjected to steam at 1800° F. FIG. 1 shows that overlaying and incorporating part of the steel surface is a bonding layer (glue layer) of chromium that is rich in chromium carbides (2). A thicker layer of metallic chromium (3) overlays this bonding layer. The chromium layer contains cracks (4) produced during the plating process, some of which formed as the plate cooled. These cracks have been filled in with chromium nitride, (5) which was formed during a nitrogen cure step. At the outer surface is a thin layer of chromium oxide (6). The various layers are not drawn to scale.

DETAILED DESCRIPTION OF THE PREFERRED EMBODIMENTS

The invention will be described hereinafter in terms of the thermal cracking of a hydrocarbon feed to produce e.g., ethylene. However, the various aspects of the invention are not intended to be limited to that embodiment. As will be apparent to those skilled in the art, they are useful in other areas of high temperature hydrocarbon processing such as both thermal and catalytic conversions of a variety of hydrocarbon feeds to produce a variety of desired products. Thus, the invention is applicable not only to ethylene crackers and their furnace tubes but also to other furnaces and furnace tubes which are exposed to carburizing or carburizing/coking environments at high temperature, such as steam reforming of hydrocarbons and the thermal cracking of hydrocarbons to produce propylene. Also, while the invention is described in terms of using chromium to produce a protective layer, molybdenum, tungsten, and mixtures thereof, with or without the use of chromium, may be used as well.

While the invention will be presented generally as a process for improved cracking of hydrocarbons, there are also other aspects of the invention. Thus, the invention relates to a method of protecting a steel portion of a reactor system that is to be contacted with hydrocarbons at elevated temperatures, and to a process for preparing a substantially crack-free or cracked-filled Group VIB metal (i.e., chromium, molybdenum or tungsten) protective surface on a steel portion of a reactor system that is to be contacted with hydrocarbons at elevated temperatures. Moreover, the invention is directed to certain Group VIB metal paints for application to a steel system for contacting hydrocarbons at elevated temperatures, and to a steel portion of a reactor system having a Group VIB metal protective layer.

Although the terms "comprises" or "comprising" are used throughout this specification, it is intended that this term encompass both the terms "consisting of", and "consisting essentially of" in the various aspects and embodiments of the present invention.

Generally, the invention is directed to a process for thermally cracking hydrocarbons. The process comprises (i) providing a carburization, abrasion and peeling resistant chromium protective layer to a steel portion of a cracking reactor system by (a) applying to the steel portion a chromium plating, cladding or other coating of chromium effective for forming a carburization resistant protective layer, to a thickness effective to isolate the steel portion from hydrocarbons during operation, and (b) forming the protective layer, anchored to the steel portion through an intermediate carbide-rich bonding layer; and then, (ii) thermally cracking a hydrocarbon feed. Preferably said thermal cracking is carded out in the presence of steam, as is well known in the art.

In one preferred embodiment, the invention is directed to a method of protecting an ethylene cracker furnace tube that is to be contacted with steam and hydrocarbons at temperatures above about 1600° F. The method comprising providing a coke-resistant chromium protective layer to an ethylene cracker tube by applying a chromium layer to at least a portion of the inner surface of a ethylene cracker tube which is made of a heat-resistant steel, and forming a metallic chromium protective layer, anchored to the steel portion through a continuous intermediate carbide-rich bonding layer.

The thickness of the chromium layer is effective to substantially isolate the iron and nickel in the steel portion from hydrocarbons during operation. The bonding layer is preferably formed by heating the applied chromium layer under conditions which prevent formation of chromium oxides.

"Reactor system" as used herein refers to a reactor for contacting with hydrocarbons at elevated temperatures, as well as associated heat exchangers, piping, etc. Preferably, the reactor system is at least one cracking furnace, including any cracking or furnace tubes thereof, effective to crack a feed material into desired products such as ethylene.

By "surfaces susceptible to carburization," there is intended at least those surfaces of the reactor system that are in contact with hydrocarbons during processing wherein carburization will take place under reaction conditions. Typically those surfaces susceptible to carburization to which protective layers according to the invention should be applied are those portions of the reactor system which exhibit skin temperatures of at least 1200° F., preferably at least 1500° F., and most preferably at least 1700° F., during operation. The higher the temperature, the more important it is to apply a protective layer.

The chromium protective layer according to the invention can be applied as a plating, cladding or other coating such as chromium-containing paint or by chemical vapor deposition. Then the plating, cladding or other coating is treated in a manner effective to form a protective layer which is anchored to the steel substrate through a continuous and uninterrupted carbide-rich bonding layer, thereby providing the necessary abrasion resistance and resistance to peeling. Preferably, the plating, cladding, or coating is resistant to abrasion, peeling or flaking for a period of 1 year, preferably 2 years, and more preferably 3 years such that the reactor system will maintain its carburization resistant properties without reapplication.

Another method of applying a metallic coating or cladding to steel is known as sputtering. For example, see U.S. Pat. No. 5,298,137 to Marshall, which describes a method and apparatus for DC linear magnetron sputtering. This and other sputtering techniques, which produce thick and even coatings of metals, can be used to apply chromium, tungsten, or molybdenum coatings to, for example, the inner surfaces of cracker furnace tubes.

It is important that the chromium be applied so that it does not readily peel off. Some methods of applying chromium, for example, methods for applying so-called "decorative chromium" plate are not suitable. These methods utilize an underlying copper or nickel layer, which can interfere with formation of the desired chromium/steel bonding layer. Also, some coating techniques are ineffective. For example, plasma spray deposition of chromium is typically ineffective as it produces a porous chromium coating, rather than a continuous coating.

Forming a protective layer suitably anchored to the steel substrate and resistant to carburization, will depend on treatment after application of the chromium. Once applied, the chromium plating, cladding or other coating should be cured at a temperature, and for a time effective to produce the intermediate carbide-rich bonding layer. For example, curing can be done at temperatures above about 1400° F., preferably above 1500° F. For example, curing at between 1700° and 1850° F. for 2 to 4 hours is effective. It is believed that the carbide-rich bonding layer is comprised mainly of carbides of chromium, although some iron and/or nickel may be present.

It is important to avoid formation of metal oxides under the carbide-rich bonding layer, so curing is preferably done in the absence of air, elemental oxygen, oxygen-containing compounds and steam. Curing results, for example, in a strongly bonded metallic protective layer preferably between 0.5 and 10 mils thick, and more preferably between 2 and 4 mils thick.

Analysis by petrographic microscopy of a cross-section of the coated and cured steel can readily determine the thickness of the protective layer. For ease of measurement of paint and coating thickness, coupons can be prepared which correspond to the coated reactor surface. These can be treated under identical conditions to the reactor system treatment. The coupons can be used to determine paint and coating thickness.

Essentially any steel can be protected according to the invention including stainless steels. Chromium platings are preferably applied to heat-resistant nickel-rich steels for better long term stability. These steels are well known in the art and typically have between about 18 and 40% Ni and between about 20 and 30% Cr. Examples of "heat-resistant" steels include HP-50 (35% Ni, 26% Cr) and HK-40 (20% Ni, 26% Cr) steels. In part, heat-resistant steels are useful because of their high temperature creep resistance.

For long term use at high temperatures, it is preferred to use a steel that inhibits diffusion of chromium from the protective layer into the steel, since significant diffusion of chromium into the steel could ultimately result in total consumption of the chromium protective layer. In this regard, it is also preferable to use heat-resistant steels, such as HP-50 and HK-40 steel. See Example 8, which shows that these steels exhibit low chromium diffusion.

It is helpful to prepare the steel surface before application of the chromium (or other Group VIB metal) so that the steel surface is clean of metal oxides (e.g., rust, chromium oxide), dirt, dust, etc., e.g. by honing or scraping the steel surface. Some surface pretreatment procedures are discussed in the Metals Handbook, Ninth Ed., Vol. 5, page 172. Furthermore, prior to applying the Group VIB metal, it is preferred to stress relieve hard steels by heating, for example, to 150°–230° C.

The thickness of the resulting chromium layer is an important factor in successfully preventing coking and carburization of ethylene cracker equipment over long time periods, such as years. Over time metals from the steel substrate (nickel and iron) can diffuse into the chromium metallic layer. The chromium coating should be thick enough to prevent the iron or nickel from migrating to the coating surface. Thus, the objective is not to merely enrich the steel surface with chromium, for example by forming a chromium/steel alloy, but rather to provide a continuous and adherent chromium metallic layer, the surface of which is substantially free of metallic iron and nickel, which increase the coke forming tendency of the coating. Thus, we have found that it is necessary that the coating thickness be at least 0.5 mils, preferably at least about 2 mils, more preferably between about 2 and 8 mils, and most preferably between about 2 and 4 mils. Also, the chromium coating should be thick enough to form a chromium carbide bonding layer after curing and still have sufficient chromium to form the metallic chromium layer. In this manner, the steel or steel portion is completely isolated from the hydrocarbon environment.

According to a preferred embodiment of a thermal cracking operation of the present invention, a diluent fluid such as steam is combined with a hydrocarbon feed such as ethane and/or propane and/or naphtha, and introduced into a cracking furnace. Within the furnace, the feed stream which has been combined with the diluent fluid will be converted to a gaseous mixture which primarily contains hydrogen, methane, ethylene, propylene, butadiene, and small amounts of heavier gases. At the furnace exit this mixture will be cooled to remove most of the heavier gases, and then compressed. The compressed mixture can then be routed through various distillation columns where the individual components such as ethylene are purified and separated.

The cracking furnace may be operated at any suitable temperature or pressure. For example, in the process of steam cracking of light hydrocarbons to ethylene, the temperature of the fluid flowing through the cracking tubes increases during processing and will attain a temperature of about 1575° F. The wall temperatures of the cracking tubes will be even higher. Furnace temperatures of nearly 2100° F. may be reached. Typical pressures for a cracking operation will generally be in the range of about 5 to about 20 psig at the outlet of the cracking tube.

One advantage of the present process is that it can be operated with less steam. Steam is traditionally added to olefin crackers. In part it is added to passivate the coking and carburization tendency of the steel. At lower steam levels, the steel becomes carburized and embrittled relatively rapidly, leading to premature failure. Using the current invention, less steam can be used, for example, to increase throughput.

Group VIB Paints

While the following discussion is primarily focused on resistant materials prepared from chromium paints, various aspects of the invention are not intended to be limited to that embodiment, but rather also encompasses other paints containing Group VIB metals.

The resistant materials can be applied in a paint-like formulation (hereinafter "paint") to a new or existing reactor system. Such a paint can be sprayed, brushed, pigged, etc. on reactor system surfaces such as stainless steels, or heat-resistant steels, and will have viscosity characteristics sufficient to provide a substantially continuous coating of measurable and substantially controllable thickness.

Preferred paints comprise Group VIB salts or compounds that melt below 2000° F., preferably below 1800° F., and more preferably below 1600° F. The group VIB metals are chromium, tungsten and molybdenum. Preferably these salts are reducible, for example with hydrogen, and thereby produce a continuous metallic phase that is resistant to coking or carburization. The invention also includes paint formulations comprising each of the other Group VIB metals, as well as for paints containing more than one Group VIB metal.

Chromium-containing paints may be advantageous as they produce a protective layer exhibiting few cracks. In fact, protective layers formed from chromium-containing paints have been observed to be relatively crackfree. Additionally, paints can be used to provide protective layers to areas not readily accessible to e.g., platings, such as welds. Paints can also be used for retrofits. Moreover, combinations of coating techniques can be used. For example, platings can be used for easily accessible areas while paints can be used for those areas not readily accessible to platings. Also, a chromium-containing paint can be applied to a newly or previously chromium plated surface to fill cracks.

The thickness of the paint after application should be between 0.5 and 15 mils, preferably 1 and 10 mils (25 and 250 microns), and more preferably between 2 and 8 mils. Thick protective layers can be built-up by successively painting and curing the steel surface.

The metallic coatings and, in particular, the paints, are preferably treated under reducing conditions with hydrogen at elevated temperatures. Additional curing can be done in the presence of hydrocarbons. In addition to applied thickness, viscosity and other properties of the paint are important. The viscosity should be such that the paint can be easily applied and that it does not drip or pool due to gravity.

One paint according to the invention comprises a Group VIB metal halide, a binding agent (binder), and optionally a solvent for thinning. Paint binding agents are well known in the art. They are used to help suspend solids to produce flowable and spreadable paints. One useful binding agent is a viscous metallic compound such as an oxygen-free organometallic compound, preferably one that is a liquid at about room temperature. It preferably has a viscosity higher than or similar to paint. Of course, it is important that the binder does not interfere with the formation of the protective layer or formation of a continuous bonding layer. Additionally, the binder or products produced from the binder should not induce coke formation.

The use of paints containing chromium halides is preferred, especially chromium chlorides ($CrCl_2$ and $CrCl_3$). Paints based on chromium halides form strongly adherent coatings. Thus, chromium chloride appears to act as a flux to clean the steel surface, and under suitable conditions decomposes to a chromium protective layer attached to the steel. One advantage of chromium coatings relative to some other coatings, such as tin coating, is that they do not result in liquid metal embrittlement of the steel.

Chromium paints are preferably reduced at high temperatures in order to produce metallic chromium-containing coatings. Useful reduction temperatures are above 1200° F., preferably at about 1400° F. or higher (e.g., 1500° F.). For example, the paint can be treated at 1400° F. in a reducing environment of 50% $H_2$, with the remainder being an inert gas, for up to 48 hours.

Chromium paints should be free of finely ground metal powder, for example, chromium powder. Chromium and some other metal powders catalyze the hydration of anhydrous $CrCl_3$. Curing of this hydrate produces chromium oxides rather than metallic coatings.

A preferred paint according to the invention comprises the following components: 1) a chromium halide, 2) a binder comprising a hydrocarbon compound or mixture, and optionally 3) a solvent. By solvent is meant a single organic compound or a mixture of organic compounds that at least partially dissolves the binder. The solvent preferably is evaporated before curing. The solvent is chosen such that the formulation is paintable. The paint can then be treated as described above to provide a chromium protective layer.

Another example of a useful paint is one comprising a fusible $CrCl_2$ or $CrCl_3$ salt which may or may not be incorporated with solvents and other additives. Other specific formulations include finely ground $CrCl_3$ in 90 wt. gear oil to form a viscous liquid, and finely ground $CrCl_3$ in a petroleum jelly carrier. Such a paint provides a simple method of applying chromium to steel, as it provides clean contact with the steel substrate which permits curing procedures to firmly attach the chromium to the steel. As an example, the paint can be reduced in $H_2$ or another suitable gas at about 1500° F. for 1 hour.

As noted above, it is important to prevent generation of chromium oxide during formation of the protective metal layer. Therefore, it is generally preferable not to include metal oxides in the paint. However, a molybdenum oxide paint is possible since that oxide melts below 1500° F., and can be reduced in-situ with hydrogen.

In a preferred embodiment, a chromium coating is prepared by reducing a paint containing anhydrous chromium (III) chloride to chromium (II) chloride, which then melts at about 1500° F. to form a molten salt film on the (steel) substrate. Reducing this film with hydrogen produces a continuous adherent chromium layer that is firmly bonded to the substrate. Achieving a continuous metallic chromium layer using a paint is difficult. In part this is because anhydrous chromium chloride is reactive, especially at elevated temperatures. Indeed, we have observed that most solvents and thickening agents will react with chromium chloride at what we call a "critical reaction temperature." This critical reaction temperature can be determined by mixing the test component with chromium chloride and then monitoring for decomposition products, such as HCl, as a function of temperature. For instance, a thermal gravimetric analysis-mass spectroscopy apparatus can be used. As an example, alkanes react with $CrCl_3$ at about 430° F. to release HCl, and form an undesirable complex, which at higher temperatures eventually forms chromium carbides. These chromium carbides appear to interfere with the reduction of chromium chloride and the formation of a continuous adherent metal chromium coating. Thus, when preparing, applying or curing a paint, it is important that the paint components do not react with the chromium chloride.

One way to prevent reaction with chromium chloride is to choose components, for example solvents, thickening agents or binders, that evaporate or decompose without interfering residues at a temperature below their critical reaction temperature. The sample is heated below the critical reaction temperature until the components evaporate or decompose, then it is heated under reduction conditions. Preferred solvents include: alcohols such as isopropanol, butanol, pentanol; liquid hydrocarbons, preferably alkanes up to about $C_{16}$; and chlorinated hydrocarbons such as dichloromethane and tfichloroethane. Preferred thickening agents include: the polymethacrylates, such as poly(methyl methacrylate), poly(ethyl methacrylate), poly(propyl methacrylate), poly(butyl methacrylate); and hydrocarbons especially paraffins such as decane, dodecane, tetradecane, hexadecane, etc. Dodecane is a preferred solvent/thickening agent.

The reactivity of chromium chloride, particularly at high temperature, also limits the choice of the process gas. The process gas must be substantially oxygen free and as dry as possible, particularly at temperatures above about 525° F.; otherwise green $Cr_2O_3$ is formed. It appears that even partial conversion of chromium chloride to the oxide can result in a chromium film that is not firmly bonded to the metal substrate. Above about 1100° F., the process gas should also be free of nitrogen to prevent chromium nitrides from forming; these also appear to interfere with the development of a continuous adherent chromium metallic coating. Useful process gases that can be used to sweep the reactor above about 1100° F. include inert gases such as helium, and argon, as well as hydrogen. Flow rates should be sufficiently high to efficiently sweep away any formed volatiles but not so high that they dislodge the halide off the steel surface. If hydrogen is used, it is important to rapidly heat the sample above the melting point of the chromium (II) halide (or any lower melting eutectic formed with the chromium halide, for example with $FeCl_2$). Otherwise, the chromium halide can reduce to the metal without melting; this can lead to a chromium metal dust rather than a continuous chromium metal coating and to poor utilization of the chromium halide. Thus it is preferred to introduce hydrogen into the process gas only at a temperature above the melting point of the chromium halide.

The time needed to reduce the chromium halide to metallic chromium depends on temperature and on hydrogen concentration. It can be easily determined by monitoring the process stream for HCl; when HCl is no longer produced, the reduction is complete. As an example of a suitable paint cure, the system including painted portions can be pressurized with argon. The reactor inlet temperature can be raised to 500° F. at a rate of 10°–100° F./hr. Hydrogen is added slowly once the temperature is between 1400° and 1600° F. These conditions can be maintained for about 48 hours. Slow heating can minimize crack formation. Curing/reduction can also be achieved in pure $H_2$ at 1300° F. to 1600° F. for 2–24 hours to develop the carbide-rich bonding layer.

For chromium-containing paints, it is preferable to also cure the paint at temperatures typically exhibited during thermal cracking. Curing temperatures between 1200° and 1800° F., preferably between 1400° and 1800° F., provide a carburization-resistant chromium protective layer anchored to a steel substrate through a carbide-rich bonding layer.

Filling of Cracks

Inevitably, cracks will appear in the chromium layer due to different thermal expansion properties of the base steel and the chromium. Therefore, in a preferred embodiment the cured plating, cladding, or other coating is then treated to fill these cracks. One method comprising contacting the coating with hydrocarbons at temperatures common to a cracking environment (e.g., about 1750° to 2050° F.), with steam addition rates reduced or minimized, or more preferably, in the absence of steam. The hydrocarbons used in this treatment step should be relatively free of impurities, preferably completely free of impurities, such as oxygen compounds, sulfur compounds, and water. Useful hydrocarbons include ethane, propane, butane, and the like. This treatment will form chromium carbides which over time (e.g. 0.5 to preferably 24 hours) will fill the cracks and effectively seal the chromium coating and carbide-rich bonding layer from later $H_2O$/steam attack during cracking.

The cured chromium carbide surface is preferably treated with steam prior to being subjected to cracking service. This steam treatment, in the absence of hydrocarbons, produces a thin chromium oxide layer over the exposed chromium carbide layer. This surface oxide layer protects the chromium carbides from attack by metal antifoulant compounds and feed impurities, such as sulfur compounds. Thus, in a further preferred embodiment, the cured and hydrocarbon-treated plating, cladding or other coating can be then treated with steam at a temperature (e.g. ≦1700° F.), and for a time effective to produce an oxide coating on the surface to be contacted with the hydrocarbons during cracking. It has been surprisingly found that at lower temperatures steam will penetrate and react with the chromium carbide that fills the cracks and the carbide-rich bonding layer, but not at higher temperatures. Thus, it is desirable that when these protective layers are contacted with steam the temperature be above 1600° F., preferably above 1700° F.

In a further embodiment for forming a protective layer, the chromium layer is bonded to steel in the presence of a nitrogen-containing compound at elevated temperature. This has the advantage of forming not only a carbide-rich bonding layer, but also results in the filling of cracks in the chromium layer with chromium nitride which effectively seals off and isolates the carbide-rich bonding layer from $H_2O$/steam attack during operations. This coated steel is especially useful in preventing carburization and metal dusting, for example in steam/ethylene crackers. Moreover, and unexpectedly, the coated and cured metal surface significantly and substantially reduces the formation of coke in ethylene cracker furnace tubes. Our experiments indicate that this coating is even better than quartz at minimizing coke formation.

When forming the protective chromium layer in the presence of a nitrogen-containing compound, curing in nitrogen gas ($N_2$) is preferred. However, other compounds having nitrogen atoms, such as ammonia or organic amines, can also be used for curing.

Heat treating the chromium coated steel in the presence of a nitrogen-containing compound is performed at temperatures between 1200° and 2000° F., preferably between 1500° and 1900° F. More preferably, curing is performed at the temperature expected at the metal wall during hydrocarbon cracking. The resulting coated steel is believed to comprise a metallic chromium protective layer, a chromium carbide bonding layer, and chromium nitride-filled cracks and voids. The Figure schematically shows this structure with an additional surface chromium oxide layer produced by contact with high temperature steam. Here the thickness of the bonding and oxide layers are exaggerated; the carbide-rich bonding layer is typically 1–2 microns thick, while the metallic chromium layer is preferably between 50 and 100 microns thick.

It is preferable to perform heat treatment in the presence of a nitrogen-containing compound before contacting the coated metal surface with hydrocarbons, especially hydrocarbons and steam, or hydrocarbons, steam and sulfur. It is also preferable to maintain the protective layer-coated steel at temperatures near the cracking temperature after heat treatment so that additional cracks are not produced.

It has been observed that the high operating temperatures used in steam cracking (1750°–1850° F.) stabilize chromium carbides and nitrides relative to chromium oxides. Conversely, at temperatures lower than about 1600° F., chromium oxides are stabilized relative to chromium carbides and nitrides. Therefore, it is preferable to maintain the protective layer-coated steel at high temperatures so that chromium oxides will not replace chromium carbides and nitrides, and the carbide-rich bonding layer will remain protected from steam attack over time. It is further preferred that the protective layer-coated steel is brought to high temperatures before adding steam, or that steam addition is minimized, preferably avoided, during curing.

The nitrogen-curing procedure is also effective for a tungsten and/or molybdenum protective layer. Mixtures of those metals with chromium can also be used. However, decoking procedures (if needed) would have to be done carefully to avoid formation of W(+6) or Mo(+6) oxides, which are volatile at temperatures above about 1200° F. Preferred decoking procedures for tungsten and molybdenum protective coatings include oxidation temperatures of below 1000° F., more preferably below 900° F., and limiting the oxygen concentration below about 20%, more preferably below about 5%.

To obtain a more complete understanding of the present disclosure, the following examples illustrating certain aspects of the invention are set forth. It should be understood, however, that the disclosure is not limited in any way to the specific details set forth therein.

In order to determine whether melt dusting has occurred, a simple burn test can be used to differentiate between thermal coke and coke produced via metal dusting or iron containing materials. According to the test, a sample of coke is heated at 1500° F. in air. Metallic coke burns brick red under these conditions, while thermal coke does not.

EXAMPLE 1

Chromium-plated steels were screened for their carburization and catalytic coking resistance in high temperature environments (e.g., 1800° F.–2000° F.). In a cracking environment of 2000° F. for 1 hour in a carburizing gas of 7% $C_3H_8$ in $H_2$ bubbled through $H_2O$, a chromium plated 304 stainless steel sample did not exhibit coking or carburization, whereas an untreated sample of INCOLOY 800, and samples of stannided, and antimonided nickel-plated INCOLOY 800 did exhibit coking.

The chromium plate was found to have reacted with the steel substrate to form a glue layer composed of chromium rich carbides overlayed with a thin metallic chromium layer and having a thin coating of chromium oxide on the exterior.

EXAMPLE 2

One environment which is particularly harsh is a halogen containing environment. The presence of halogens adversely affects raw steels. The chromium protective layers of the invention are surprisingly effective for isolating the steels from those halogen effects at high temperatures. The protective layers of the invention are effective at even high halogen concentrations.

The following tests were run to demonstrate the effectiveness of chromium protective layers for isolating underlying metallurgy from halogen containing environments. The tests were done in a Lindberg quartz tube furnace. Samples of stainless steel, provided with stannide protective layers and chromium protective layers, were tested at 1000° F. and 1200° F. for twenty-one hours, in the presence of methylchloride. The coupons were placed in an open quartz boat within the hot zone of a tube furnace. The tube was flushed with nitrogen for a few minutes. Then the samples were exposed to a hydrocarbon gas. For experiments using 10,000 ppm halogen the gas was 1% $CH_3Cl$ in hydrogen. For those using 1,000 ppm halogen the gas was a mixture of 0.1% $CH_3Cl$ and 7% propane in hydrogen. Gas flows were 25 to 30 cc/min. at atmospheric pressure. The samples were rapidly brought to operating temperatures.

The test results are shown in the following Table. A "pass" result means the samples did not substantially form coke on the metal surface.

TABLE

Effect of Chloride

| Ex. No. | Amount of MeCl, ppm | Temp., °F. | Raw Steel | Stannide Protective Layer | Chromium Protective Layer |
|---|---|---|---|---|---|
| 1 | 10,000 | 1000 | Fail | Pass | Pass |
| 2 | 10,000 | 1200 | Fail | Fail | Pass |
| 3 | 1,000 | 1200 | Fail | Pass | Pass |

The results show that both chromium and stannide protected steel can withstand high halogen concentrations at 1000° F., but the stannided protective layer is not as effective at 1200° F. Chromium protective layers were effective under all conditions tested.

EXAMPLE 3

Dry carburization tests were run using 7% $C_3H_8$ in $H_2$ over HP-50 steel chips in a Lindberg Quartz tube furnace. The results were:

| | Cr "Paint"* on HP50 | Cr Plate** on HP50 | Untreated HP50 |
|---|---|---|---|
| 1600° F. 4 Hrs | Trace of coke Uncarburized | Essentially coke free Uncarburized | Coked Carburized |
| 2000° F. 2 Hrs | Trace of coke Uncarburized | Substantially coke free Uncarburized | Coked Carburized |

*$CrCl_2$ powder on HP-50 reduced 2 hrs. at 1500° F. in $H_2$
**Commercial hard Cr plate on HP-50 heat treated in $H_2$ at 1500° F. for 2 hrs.

Microscopic analysis revealed a chromium-carbide bonding layer between the chromium coatings and the underlying steel in the chromium-treated samples. The untreated HP-50 showed deep and intense carburization.

EXAMPLE 4

Wet coking and carburization tests were run using 7% $C_3H_8$ in $H_2$ bubbled through water in a Lindberg Quartz tube furnace. The tests were done over Cr-plated steel. The results were:

|  | Cr Plate** on HP50 | Untreated HP50 |
| --- | --- | --- |
| 1600° F. 4 Hrs | Coke free Uncarburized | Coked Lightly carburized |
| 2000° F. 2 Hrs | Essentially coke free Uncarburized | Coked Lightly carburized |

This example shows that, compared to Example 3, steam inhibits carburization. Microscopic analysis of the chromium-treated steel after the tests revealed a chromium-carbide bonding layer between the chromium metal coating and the underlying steel in the chromium-treated sample. This layer was thicker in the higher temperature experiment. Some chromium oxide was observed on the exterior surface and within the natural cracks of the chromium plate.

EXAMPLE 5

An HP-50 steel chip was treated with $CrCl_2$ powder and cured in pure $H_2$ at 1500° F. for 1 hour. Microscopic analysis revealed that the chip had a high quality, continuous, uniformly thick, and firmly and cleanly attached coating of chromium, 1 mil in thickness.

EXAMPLE 6

Two INCOLOY 800 steel chips were placed in a quartz sample boat. The first had been treated with a mixture of about equal amounts of $CrCl_2$ and $MoCl_5$ powders. The second chip (downstream from the first) had been treated with a mixture of $CrCl_2$ and $WCl_6$ powders. Pure $H_2$ gas was passed over the samples in a Lindberg quartz tube furnace at 1200° F. for two hours. Microscopy analysis revealed that the first chip had a metallic coating 1–2 microns thick of chromium with about 7% Mo. The second chip had received a 1 micron coating of chromium with about 20% W and 10% Mo.

This experiment demonstrates that mixed metal coatings can be prepared from mixtures of metal salts. The molybdenum and tungsten chlorides are volatile; nonetheless, the molybdenum and tungsten were incorporated into the metallic coating.

EXAMPLE 7

An HP-50 steel chip was coated with a mixture of finely ground $CrCl_3$ crystals in just enough petroleum jelly to make a viscous paint. The coated chip was cured in $H_2$ at 1500° F. for 1 hour. Microscopic analysis of a cross-section revealed a uniform coating of chromium metal, tightly interlocked with a similarly thick, carbide-rich bonding layer onto the underlying steel.

EXAMPLE 8

Sample chips of chromium-plated 9 chromium 1 Mo steel, 304 stainless steel, and HP-50 steel were placed in a quartz sample boat and treated in dry nitrogen for two hours at 1800° F. in a quartz tube furnace. Petrographic microscopy analysis revealed no evidence of peeling of the chromium plate from any of the steel samples and, in no case was there significant diffusion of iron or nickel into the chromium protective layer. Moreover, distinctive carbide-rich bonding layers were observed in all of the samples.

For example, with the chromium-plated 9 chromium 1 Mo steel, a single carbide layer formed between the chromium plate and the underlying steel. Three layers formed between the chromium plate and the 304 stainless steel: chromium ferride on the steel itself, followed successively by an iron-rich carbide and a chromium-rich carbide. Two chromium-rich carbide layers formed on the chromium-plated HP-50 steel: an inner layer containing nickel, and a nearly nickel-free outer layer.

Under the conditions of this test, no significant diffusion of chromium from the protective layer into the HP-50 steel was observed. However, there was extensive diffusion of chromium from the protective layer into the underlying 9 chromium 1 Mo steel, and some chromium diffusion was detected from the protective layer into the type 304 stainless steel. While the chromium-coated HP-50 steel may be preferred for use at high temperatures due to the resistance of chromium migration from the protective layer into the steel, the chromium-coated 9 chromium 1 Mo steel and type 304 stainless steel may be used advantageously in lower temperature environments.

Chromium nitride also formed as a coating on the surface of the chromium metal in all samples, as well as filling and sealing cracks that formed upon heating the chromium plates. The crack-filling chromium nitride was found to persist after exposure to pure hydrogen for an additional two hours at 1800° F.

EXAMPLE 9

The nitrided sample chips of chromium plated HP-50 steel of Example 8 were tested for coking and carburization in the presence of water and sulfur. These tests were run in a Lindberg Quartz tube furnace using 7% $C_3H_8$ in $H_2$. Sulfur (100 ppm) as $CS_2$ was added to the gas, which was then bubbled through water. The results were, that after 4 hours at 1800° F., the nitrided chromium plated HP-50 was essentially coke free. In contrast, the untreated HP-50 was coked.

EXAMPLE 10

A Chromium Plated HP-50 Steel

A section of a furnace tube made of HP-50 Steel was cleaned and then electroplated to produce a hard chromium coating. The thickness of the coating was between 75 and 100 microns. This section was welded into the furnace tube in an ethylene cracking unit.

After cracking ethane to ethylene at about 1800° F., in the presence of steam and added sulfur, this tube section has lower coking tendencies than the uncoated HP-50 steel sections.

EXAMPLE 11

Chromium Plated and Heat Treated HP-50 Steel

A section of a furnace tube made of HP-50 Steel was cleaned and then electroplated to produce a hard chromium coating. The thickness of the coating was between 75 and 100 microns. This section was welded into the furnace tube in an ethylene cracking unit, and then heated to 1500° F. in oxygen-free argon for 4 hrs. (Hydrogen heat treatment can also be used). After cracking ethane to ethylene at about 1800° F., in the presence of steam and added sulfur, this tube section has lower coking tendencies than the uncoated HP-50 steel sections and the chromium layer does not readily peel off.

EXAMPLE 12

Filling Cracks by Carbiding A Chromium Plated HP-50 Steel

A section of a furnace tube made of HP-50 Steel was cleaned and then electroplated to produce a hard chromium coating. The thickness of the coating was between 75 and 100 microns. This section is heated in hydrogen to 1600° F. and then treated with oxygen-free, water-free ethane for 4 hrs. This section is welded into the furnace tube in an ethylene cracking unit.

After cracking ethane to ethylene at about 1800° F., in the presence of steam and added sulfur, this tube section has lower coking tendencies than the uncoated HP-50 steel sections and the chromium layer does not readily peel off.

EXAMPLE 13

Filling Cracks by Nitriding A Chromium Plated HP-50 Steel

A section of a furnace tube made of HP-50 Steel was cleaned and then electroplated to produce a hard chromium coating. The thickness of the coating was between 75 and 100 microns. This section is heated to 1600° F. and is then treated with an oxygen-free, water-free nitrogen atmosphere for 4 hrs. This section is welded into the furnace tube in an ethylene cracking unit.

After cracking ethane to ethylene at about 1800° F., in the presence of steam and added sulfur, this tube section has lower coloring tendencies than the uncoated HP-50 steel sections and the chromium layer does not readily peel off.

EXAMPLE 14

Preparing an Chromium Paint and Coating Steel

Finally divided chromium (III) chloride, $CrCl_3$ was prepared by ball milling flake $CrCl_3$ under isopropanol for 2 days. The solvent was then allowed to evaporate and the finely divided chromium chloride was dried at 300° F. No green chromium oxide was observed.

The finely divided chromium (III) chloride was dispersed into a sufficient quantity of dodecane to make a flowable paint (if this material is to be spray-painted it can be thinned with a lower boiling solvent, such as hexane, octane, methylene chloride, isopropanol, etc.). The paint was then spread on a 316 stainless steel tube, and placed in a quartz tube in a furnace. The tube was continuously purged with high purity argon, while the sample was slowly heated to 400° F. to allow for the complete evaporation of dodecane. After a 2 hour hold at 400° F., the temperature was quickly ramped up to 1525° F. At this point the argon purge stream was gradually replaced by hydrogen over a 10 minute period. The sample was then heated under pure hydrogen for 2 hours to form a continuous adherent chromium coating.

EXAMPLE 15

Preparing an Chromium Paint and a Chromium Coating

A poly(butyl methacrylate) based paint was prepared by dissolving 0.33 grams of poly(butyl methacrylate) in 6.0 grams of methyl ethyl ketone, and then adding 2.97 grams of the finely divided chromium (III) chloride of example 1. The paint was blotted onto HP-50 steel, which was then placed in a quartz tube and heated to 450° F. under flowing high purity helium. After a 1 hour hold, the temperature was gradually increased at 5° F./min to 650° F. and held there for 3 hours. Then the temperature was rapidly increased to 1525° F., and the helium was replaced within hydrogen over 10 minutes. After 2 hours the furnace was turned off, and the sample cooled to room temperature. A bright shiny adherent coating of metallic chromium was seen.

COMPARATIVE EXAMPLE 16

Chromium Chloride Reduction in the Presence of Nitrogen

This example followed the procedures of example 15, except that nitrogen gas was used instead of helium. After cooling to room temperature, the sample was removed from the furnace to reveal a dark gray powder, which could be easily brushed off the surface. X-ray diffraction showed that the powder was mainly $Cr_2N$ and $CrN$.

COMPARATIVE EXAMPLE 17

Overly Rapid Heating

This example followed the procedures of example 15, except that the sample was rapidly heated from 450° F. to 1525° F. This apparently did not allow adequate time for the poly(butyl methacrylate) to decompose. The resulting dark gray powder was loosely attached to the surface and could easily be brushed off.

While the invention has been described above in terms of preferred embodiments, it is to be understood that variations and modifications may be used as will be appreciated by those skilled in the art. Essentially, therefore, there are many variations and modifications to the above preferred embodiments which will be readily evident to those skilled in the art and which are to be considered within the scope of the invention as defined by the following claims.

What is claimed is:

1. A steel portion of a reactor system in contact with steam and hydrocarbons, said steel portion having a Group VIB metal protective layer and at least one intermediate, carbide-rich, bonding layer, wherein said protective layer is substantially free of unfilled cracks or Group VIB oxides extending to said bonding layer, wherein the protective layer is formed by bonding a Group VIB metal layer to steel in the presence of a nitrogen-containing compound at a temperature effective to form the carbide-rich bonding layer and to fill cracks in the Group VIB metal layer with Group VIB metal nitride which effectively seals off and isolates the Group VIB carbide-rich bonding layer from later $H_2O$/steam attack.

2. A steel portion according to claim 1, wherein the nitrogen-containing compound is nitrogen gas.

3. A steel portion according to claim 1, wherein the temperature effective to form the bonding layer and to fill cracks is in the range of from about 1200° to 2000° F.

4. A steel portion according to claim 1, wherein the temperature effective to form the bonding layer and to fill cracks is at least 1500° C.

5. A steel portion according to claim 1, wherein the thickness of the carbide-rich bonding layer is in the range from about 1–2 microns and the thickness of the Group VIB metallic layer is in the range from about 50 to 100 microns.

6. A steel portion according to claim 1, wherein the Group VIB metal is chromium.

* * * * *